(12) United States Patent
Boaz

(10) Patent No.: US 8,613,940 B2
(45) Date of Patent: Dec. 24, 2013

(54) CARBONATE DERIVATIVES AS SKIN CARE

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/975,562

(22) Filed: Dec. 22, 2010

(65) Prior Publication Data

US 2012/0059056 A1 Mar. 8, 2012

Related U.S. Application Data

(60) Provisional application No. 61/379,929, filed on Sep. 3, 2010.

(51) Int. Cl.
*A61K 31/265* (2006.01)
*A61K 6/02* (2006.01)
*C07C 69/96* (2006.01)

(52) U.S. Cl.
USPC .......................... 424/401; 514/512; 558/268

(58) Field of Classification Search
None
See application file for complete search history.

(56) References Cited

U.S. PATENT DOCUMENTS

| | | |
|---|---|---|
| 4,107,290 A | 8/1978 | Jacquet et al. |
| 5,605,933 A | 2/1997 | Duffy et al. |
| 5,972,323 A | 10/1999 | Lang et al. |
| 6,572,882 B1 | 6/2003 | Vercauteren et al. |
| 7,030,265 B2 | 4/2006 | Sin et al. |
| 7,098,246 B2 | 8/2006 | Geelings et al. |
| 7,102,019 B2 | 9/2006 | Streicher et al. |
| 7,670,606 B2 | 3/2010 | Volkmann |
| 7,671,009 B2 | 3/2010 | Ludin et al. |
| 8,029,810 B2 | 10/2011 | Skold |
| 8,324,270 B2 | 12/2012 | Maeda et al. |
| 2003/0225160 A1 | 12/2003 | Geerlings et al. |
| 2005/0015058 A1 | 1/2005 | Millerd |
| 2005/0095232 A1 | 5/2005 | Volkmann |
| 2009/0035236 A1 | 2/2009 | Maes et al. |
| 2009/0035237 A1 | 2/2009 | Maes et al. |
| 2009/0035240 A1 | 2/2009 | Maes et al. |
| 2009/0035242 A1 | 2/2009 | Maes et al. |
| 2009/0035243 A1 | 2/2009 | Czarnota et al. |
| 2009/0068132 A1 | 3/2009 | Bratescu et al. |
| 2012/0029198 A1 | 2/2012 | Deng et al. |

FOREIGN PATENT DOCUMENTS

| | | |
|---|---|---|
| DE | 2311346 A1 | 10/1973 |
| DE | 4415204 A1 | 11/1995 |
| EP | 0342055 A2 | 11/1989 |
| EP | 1498104 A1 | 1/2005 |
| EP | 2072494 A1 | 6/2009 |
| ES | 2233208 A1 | 6/2005 |
| ES | 2246603 A1 | 2/2006 |
| FR | 2436602 A1 | 4/1980 |
| FR | 2919800 A1 | 2/2009 |
| JP | 2002/193752 A | 7/2002 |
| JP | 2005/041871 A | 2/2005 |
| WO | WO 95/16659 A1 | 6/1995 |
| WO | WO 97/20812 A1 | 6/1997 |
| WO | 02055540 A1 | 7/2002 |
| WO | WO 2004/054992 A1 | 7/2004 |
| WO | WO 2005/019156 A2 | 3/2005 |
| WO | WO 2005/108534 A1 | 11/2005 |
| WO | WO 2007/053794 A2 | 5/2007 |
| WO | WO 2009/018389 A1 | 2/2009 |
| WO | WO 2009/156324 A2 | 12/2009 |
| WO | WO 2011/041487 * | 4/2011 |
| WO | WO 2011/041487 A1 | 4/2011 |

OTHER PUBLICATIONS

Buisman, G. J. H. et al.; "Enzymatic esterifications of functionalized phenols for the synthesis of lipophilic antioxidants"; Biotechnology Letters, vol. 20, No. 2, Feb. 1998, pp. 131-136.
Gordon, Michael H. et al.; "Antioxidant Activity of Hydroxytyrosol Acetate Compared with That of Other Olive Oil Polyphenols"; Journal of Agricultural and Food Chemistry, 49, 2001, pp. 2480-2485.
Grasso, Salvatore et al.; "Hydroxytyrosol lipophilic analogues: Enzymatic synthesis, radical scavenging activity and DNA oxidative damage protection"; Bioorganic Chemistry, 35, 2007, pp. 137-152.
Mateos, Raquel et al.; "New Lipophilic Tyrosyl Esters. Comparative Antioxidant Evaluation with Hydroxytyrosyl Esters"; Journal of Agricultural and Food Chemistry, 56, 2008, pp. 10960-10966.
Trujillo, Mariana et al.; "Lipophilic Hydroxytyrosyl Esters. Antioxidant Activity in lipid Matrices and Biological Systems." Journal of Agricultural and Food Chemistry, 54, 2006, pp. 3779-3785.
Kim, Sungbum, et al., "Synthesis and in vitro biological activity of retinyl polyhydroxybenzoates, novel hybrid retinoid derivatives." Bioorganic & Medicinal Chemistry Letters 19, (2009), pp. 508-512.
Co-pending U.S. Appl. No. 13/031,375, filed Feb. 21, 2011, Neil Warren Boaz.
Notification of Transmittal of the International Search Report and the Written Opinion of the International Searching Authority, or the Declaration with date of mailing Nov. 17, 2011 for International Application No. PCT/US2011/049047.
Chankeshwara, Sunay V., et al., "Organocatalytic Methods for Chemoselective O-tert-Butoxycarbonylation of Phenols and Their Regeneration from the O-t-Box Derivatives", The Journal of Organic Chemistry, vol. 73, No. 21 (2008), pp. 8615-8618.
Kittisak, Likhitwitayawuid, et al., "Structure Modification of Oxyresveratol for tyrosinase inhibitory activity", Researches Assisted by the Asahi Glass Foundation, Reports, XX, JP, (2008) p. 60. (Abstract).
Charvat, Trevor T., et al., "Design, synthesis, and biological evaluation of chicoric acid analogs as inhibitors of HIV-1 integrase", Bioorganic & Medicinal Chemistry 14 (2006) pp. 4552-4567.

(Continued)

Primary Examiner — Alicia L Otton
(74) Attorney, Agent, or Firm — Jennifer R. Knight; Polly C. Owen

(57) ABSTRACT

Carbonates of anti-aging ingredients, in particular anti-oxidants and skin illuminating phenol ingredients, have been prepared as derivatives of these ingredients with enhanced physical properties. It has been demonstrated that these carbonates will hydrolyze under enzymatic catalysis to release the parent ingredient. In contrast, esters of the phenolic groups in many cases do not hydrolyze under the same conditions.

15 Claims, No Drawings

(56) References Cited

OTHER PUBLICATIONS

Bratt, Mark O., et al., "Synthesis of Carbonates and Related Compounds from Carbon Dioxide via Methanesulfonyl Carbonates", Journal of Organic Chemistry, American Chemical Society, Easton.; US, vol. 68, No. 14, (2003), pp. 5439-5444.

Dikusar, E. A., et al., "Methyl-and Ethyl Carbonates Derived from Vanillin and Vanillal in the Synthesis of Nitrogen-containing Compounds", Russian Journal of General Chemistry, vol. 77, No. 5, (2007), pp. 905-910.

Jones, Ryan M., et al., "Rapid Syntheses of Benzopyrans from o-OBOC Salicylaldehydes and Salicyl alcohols: A Three-Component Reaction", The Journal of Organic Chemistry, vol. 67, No. 20, (2002), pp. 6911-6915.

Carafa, Marianna, et al., "Superbase-promoted direct N-carbonylation of pyrrole with carbonic acid diesters", Tetrahedron Letters, Elsevier, Amsterdam, NL, vol. 49, No. 22, (2008), pp. 3691-3696.

Hirakawa, Takuya, et al., "A Magentically Separable Heterogeneous Deallylation Catalyst: [CpRu($n^3$-$C_3H_5$)(2-pyridinecarboxylato)]$PF_6$ Complex Supported on a Ferromagnetic Microsize Particle $Fe_3O_4$@$SiO_2$", European Journal of Organic Chemistry, vol. 2009, No. 6, (2009), pp. 789-792.

Hallman, Kristina, et al., "Enantioselective allylic alkylation using polymer-supported palladium catalysts", Tetrahedron: Asymmetry, vol. 10, No. 20, (1999), pp. 4037-4046.

Ouchi, Hidekazu, et al., "1-tert-Butoxy-2-tert-butoxycarbonyl-1,2-dihydroisoquinoline: A Novel and Chemoselective tert-Butoxycarbonylation Reagent", Organic Letters, vol. 4, No. 4 (2002), pp. 585-587.

Cuny, Gregory D., et al., "Solution-Phase Ring Opening Cross-Metathesis of Bicyclic Alkenes with Styrene Derivatives and Its Application to "Resin Capture" Solid-Phase Synthesis", Tetrahedron, Elsevier Science Publishers, Amsterdam, NL, vol. 55, No. 27, (1999), pp. 8169-8178.

Maugard, T., et al: "Study of Vitamin Ester Synthesis by Lipase-Catalyzed Transesterification in Organic Media"; Biotechnology Progress, vol. 16, No. 3, (2000), pp. 358-362.

Maugard, Thierry and Legoy, Marie Dominique; "Enzymatic Synthesis of Derivatives of Vitamin A in Organic Media"; Journal of Molecular Catalysis B: Enzymatic 8; 2000; pp. 275-280.

Maugard, Thierry et al; "Synthesis of Water-Soluble Retinol Derivatives by Enzymatic Method"; Biotechnol. Prog.; 2002; vol. 18; pp. 424-428.

O'Connor, Charmian J. et al; "Candida Cylindracea Lipase-Catalysed Synthesis of Retiny and Oleyl Palmitates; Carbon ChainLength Dependence of Esterase Activity"; Aust. J. Chem.; 1992; vol. 45; pp. 641-649.

Stryer, Lubert; "Acetoacetate is a Major Fuel in Some Tissues"; Biochemistry, Fourth Edition; 1995; Chapter 24, p. 613.

Co-pending U.S. Appl. No. 61/368,850, filed Jul. 29, 2012; Liu Deng.

Notification of Transmittal of the International Search report and Written Opinion of the International Searching Authority, or the Declaration with date of mailing Sep. 23, 2011 for International Application No. PCT/US2011/045303.

Notice of Allowance dated May 1, 2012 from the USPTO for U.S. Appl. No. 13/031,375.

Notification of Transmittal of the International Search Report and Written Opinion of the International Searching Authority, or the Declaration with date of mailing May 31, 2012 for International Application No. PCT/US2012/025335.

Database Registry [Online], Chemical Abstracts Service, Columbus, Ohio, US; Jun. 8, 2008, XP002676266, Database accession No. 1026294-10-9 abstract.

USPTO Office Action dated Aug. 3, 2012 for co-pending U.S. Appl. No. 12/975,572.

USPTO Notice of Allowance dated Aug. 14, 2012 for co-pending U.S. Appl. No. 13/031,375.

USPTO Office Action dated Nov. 14, 2012 for co-pending U.S. Appl. No. 12/975,572.

USPTO Office Action dated Dec. 27, 2012 for co-pending U.S. Appl. No. 12/975,572.

USPTO Office Action dated May 3, 2013 for co-pending U.S. Appl. No. 12/975,572.

\* cited by examiner

CARBONATE DERIVATIVES AS SKIN CARE

CROSS REFERENCES TO RELATED APPLICATIONS

This application is an original application claiming priority to provisional application U.S. Ser. No. 61/379,929 filed Sep. 3, 2010, herein incorporated by reference to the extent it does not contradict the statements herein.

FIELD OF THE INVENTION

The present invention pertains to the field of alkyl carbonates of anti-aging ingredients, such as antioxidants and skin illuminating phenol ingredients. The present invention also pertains to processes for producing alkyl carbonates.

BACKGROUND OF THE INVENTION

A large number of anti-aging skin care ingredients are phenolic in nature. Many of these function as anti-oxidants or skin illuminating ingredients, and the free hydroxyl groups are key to the redox activity of these species. Unfortunately, many of these materials have physical properties that are not well-suited for use as cosmetic ingredients; they tend to have minimal solubility in most cosmetic solvents (both oils and water) and can be unstable in a cosmetic formulation (particularly towards oxidation). Derivatization of the phenolic groups can stabilize these materials. However, these derivatives must be readily removable under physiological conditions to liberate the phenolic groups to afford the desired anti-aging activity (Grasso et al, *Bioorganic Chem.* 2007, 35, 137-152).

Derivatization of the phenolic groups can vastly improve the physical properties of these materials. One useful method for derivatization of hydroxyl or carboxyl-containing materials is to prepare esters of these materials. The usefulness of this approach often depends upon the ability of enzymes in the skin to hydrolyze these esters to liberate the parent active. This strategy is effective for the derivatization of many active ingredients containing aliphatic alcohols, but esters derived from phenols are often refractive or only slowly reactive towards enzymatic hydrolysis. Despite this, there has been interest in ester derivatives of phenolic active ingredients such as resveratrol (composition of matter patents: U.S. Pat. No. 6,572,882 and US Patent Appl 2009/0068132 A1; formulation patents: US Patent Appl 2009/0035236 A1, US Patent Appl 2009/0035237 A1, US Patent Appl 2009/0035240 A1, US Patent Appl 2009/0035242 A1, and US Patent Appl 2009/0035243 A1) and hydroxytyrosol (U.S. Pat. No. 7,098,246 and US Patent Appl 2003/0225160), even though the hydrolysis to release the parent phenolic active ingredient is questionable. Indeed, with hydroxytyrosol the aliphatic hydroxyl group is often the only functionality esterified (Grasso et al, *Bioorganic Chem.* 2007, 35, 137-152; Trujillo et al, *J. Agric. Food Chem.* 2006, 54, 3779-3785; Mateos et al, *J. Agric. Food Chem.* 2008, 56, 10960-10966; Gordon et al, *J. Agric. Food Chem.* 2001, 49, 2480-2485; Buisman et al, *Biotechnology Lett.* 1998, 20, 131-136; US Patent Appl 2005/015058 A1; Fr. Demande 2,919,800; ES 2,233,208; ES 2,246,603), leaving the phenolic groups underivatized, which will not improve the stability of the catechol functionality. Alkyl carbonate derivatives of these phenolic skin care active ingredients have not been described.

Novel derivatives of phenolic actives that will hydrolyze under physiological (enzymatic) conditions would be of great utility and interest.

SUMMARY OF THE INVENTION

In one embodiment of the invention, an alkyl carbonate is provided having the general structure 1:

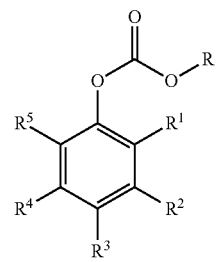

wherein R is selected from substituted and unsubstituted, branched- and straight-chain, saturated, unsaturated, and polyunsaturated $C_1$-$C_{22}$ alkyl. and $R^1$, $R^2$, $R^3$, $R^4$, and $R^5$ are independently selected from hydrogen, substituted and unsubstituted, branched- and straight-chain saturated, $C_4$-$C_{22}$ alkyl, substituted and unsubstituted, branched- and straight-chain $C_2$-$C_{22}$ alkenyl, substituted and unsubstituted, branched- and straight-chain $C_2$-$C_{22}$ alkynyl, substituted and unsubstituted, branched- and straight-chain $C_4$-$C_{22}$ dienyl, substituted and unsubstituted, branched- and straight-chain $C_6$-$C_{22}$ trienyl, $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$-alkanoyloxy, hydroxy, aryl, heteroaryl, thiol, thioether, and halogen.

In another embodiment of the invention, a process is provided for producing an alkyl carbonate having the general structure 1:

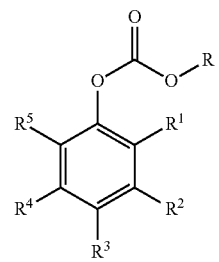

wherein R is selected from substituted and unsubstituted, branched- and straight-chain, saturated, unsaturated, and polyunsaturated $C_1$-$C_{22}$ alkyl. and $R^1$, $R^2$, $R^3$, $R^4$, and $R^5$ are independently selected from hydrogen, substituted and unsubstituted, branched- and straight-chain saturated, $C_4$-$C_{22}$ alkyl, substituted and unsubstituted, branched- and straight-chain $C_2$-$C_{22}$ alkenyl, substituted and unsubstituted, branched- and straight-chain $C_2$-$C_{22}$ alkynyl, substituted and unsubstituted, branched- and straight-chain $C_4$-$C_{22}$ dienyl, substituted and unsubstituted, branched- and straight-chain $C_6$-$C_{22}$ trienyl, $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$-alkanoyloxy, hydroxy, aryl, heteroaryl, thiol, thioether, and halogen, comprising reacting at least one alcohol of Formula 4:

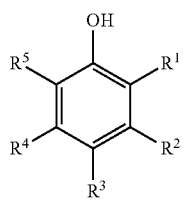

with a chloroformate, bromoformate, or dicarbonate to produce said alkyl carbonate of Formula 1.

DETAILED DESCRIPTION

In this invention, novel alkyl carbonates of phenolic anti-aging skin care ingredients have been discovered of the general structure 1:

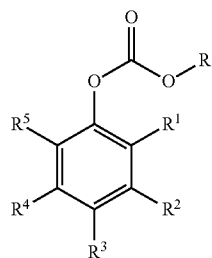

wherein

R is selected from substituted and unsubstituted, branched- and straight-chain, saturated, unsaturated, and polyunsaturated $C_1$-$C_{22}$ alkyl; and $R^1$, $R^2$, $R^3$, $R^4$, and $R^5$ are independently selected from hydrogen; substituted and unsubstituted, branched- and straight-chain saturated, $C_4$-$C_{22}$ alkyl; substituted and unsubstituted, branched- and straight-chain $C_2$-$C_{22}$ alkenyl; substituted and unsubstituted, branched- and straight-chain $C_2$-$C_{22}$ alkynyl; substituted and unsubstituted, branched- and straight-chain $C_4$-$C_{22}$ dienyl; substituted and unsubstituted, branched- and straight-chain $C_6$-$C_{22}$ trienyl; $C_1$-$C_6$-alkoxy; carboxyl; $C_1$-$C_{15}$ aminocarbonyl; $C_1$-$C_{15}$ amido; cyano; $C_2$-$C_{15}$-alkoxycarbonyl; $C_2$-$C_{15}$-alkoxycarbonyloxy; $C_2$-$C_{15}$-alkanoyloxy; hydroxyl; aryl; heteroaryl; thiol; thioether; and halogen. The terms "$C_1$-$C_6$-alkoxy", "$C_2$-$C_{15}$-alkoxycarbonyl", "$C_2$-$C_{15}$-alkoxycarbonyloxy", and "$C_2$-$C_6$-alkanoyloxy" are used to denote radicals corresponding to the structures —$OR^6$, —$CO_2R^7$, —$OCO_2R^7$, and —$OCOR^7$, respectively, wherein $R^6$ is $C_1$-$C_6$ straight or branched, substituted or unsubstituted alkyl and $R^7$ is $C_1$-$C_{14}$ straight or branched, substituted or unsubstituted alkyl. The terms "$C_1$-$C_{15}$-aminocarbonyl" and "$C_1$-$C_{15}$ amido" are used to denote radicals corresponding to the structures —NHCOR$^8$, —CONHR$^8$, respectively, wherein $R^8$ is $C_1$-$C_{15}$ straight or branched, substituted or unsubstituted alkyl. Any two or more of the adjoining $R^1$, $R^2$, $R^3$, $R^4$, and $R^5$ can be connected to form one or more fused rings.

The saturated, unsaturated, and polyunsaturated groups, which may be represented by R, may be straight- or branched-chain aliphatic hydrocarbon radicals containing up to about 22 carbon atoms and may be substituted, for example, with one to three groups selected from $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$-alkoxycarbonyloxyaryl, $C_2$-$C_{15}$-alkanoyloxy, hydroxy, aryl, substituted aryl, heteroaryl, substituted heteroaryl, thiol, thioether, and halogen. The terms "$C_1$-$C_6$-alkoxy", "$C_2$-$C_{15}$-alkoxycarbonyl", "$C_2$-$C_{15}$-alkoxycarbonyloxy", and "$C_2$-$C_6$-alkanoyloxy" are used to denote radicals corresponding to the structures —$OR^6$, —$CO_2R^7$, —$OCO_2R^7$, and —$OCOR^7$ respectively, wherein $R^6$ is $C_1$-$C_6$ straight or branched, substituted or unsubstituted alkyl and $R^7$ is $C_1$-$C_{14}$ straight or branched, substituted or unsubstituted alkyl. The terms "$C_1$-$C_{15}$-aminocarbonyl" and "$C_1$-$C_{15}$ amido" are used to denote radicals corresponding to the structures —NHCOR$^8$, —CONHR$^8$, respectively, wherein $R^8$ is $C_1$-$C_{15}$ straight or branched, substituted or unsubstituted alkyl. The term "$C_2$-$C_{15}$-alkoxycarbonyloxyaryl" is used to denote radicals corresponding to the structures —Ar—OCOOR$^9$, wherein $R^9$ is a $C_1$-$C_{14}$ alkyl or substituted $C_1$-$C_{14}$ alkyl.

The alkyl, alkenyl, alkynyl, dienyl, and trienyl groups, which may be represented by $R^1$, $R^2$, $R^3$, $R^4$, and $R^5$, may be straight- or branched-chain aliphatic hydrocarbon radicals containing up to about 22 carbon atoms and may be substituted, for example, with one to three groups selected from $C_1$-$C_6$-alkoxy, carboxyl, $C_1$-$C_{15}$ aminocarbonyl, $C_1$-$C_{15}$ amido, cyano, $C_2$-$C_{15}$-alkoxycarbonyl, $C_2$-$C_{15}$-alkoxycarbonyloxy, $C_2$-$C_{15}$-alkoxycarbonyloxyaryl, $C_2$-$C_{15}$-alkanoyloxy, hydroxy, aryl, substituted aryl, heteroaryl, substituted heteroaryl, thiol, thioether, and halogen. The terms "$C_1$-$C_6$-alkoxy", "$C_2$-$C_{15}$-alkoxycarbonyl", "$C_2$-$C_{15}$-alkoxycarbonyloxy", and "$C_2$-$C_6$-alkanoyloxy" are used to denote radicals corresponding to the structures —$OR^6$, —$CO_2R^7$, —$OCO_2R^7$, and —$OCOR^7$, respectively, wherein $R^6$ is $C_1$-$C_6$ straight or branched, substituted or unsubstituted alkyl and $R^7$ is $C_1$-$C_{14}$ straight or branched, substituted or unsubstituted alkyl. The terms "$C_1$-$C_{15}$-aminocarbonyl" and "$C_1$-$C_{15}$ amido" are used to denote radicals corresponding to the structures —NHCOR$^8$, —CONHR$^8$, respectively, wherein $R^8$ is $C_1$-$C_{15}$ straight or branched, substituted or unsubstituted alkyl. The term "$C_2$-$C_{15}$-alkoxycarbonyloxyaryl" is used to denote radicals corresponding to the structures —Ar—OCOOR$^9$, wherein $R^9$ is a $C_1$-$C_{14}$ alkyl or substituted $C_1$-$C_{14}$ alkyl.

The aryl groups which may be present as substituents on R, $R^1$, $R^2$, $R^3$, $R^4$, and $R^5$ may include phenyl, naphthyl, or anthracenyl and phenyl, naphthyl, or anthracenyl substituted with one to three substituents selected from $C_1$-$C_6$-alkyl, substituted $C_1$-$C_6$-alkyl, $C_6$-$C_{10}$ aryl, substituted $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_{15}$-alkoxycarbonyl, $C_2$-$C_{15}$-alkoxycarbonyloxy, $C_2$-$C_{15}$-alkanoylamino and —O—$R^{10}$, —S—$R^{10}$, —$SO_2$—$R^{10}$, —NHSO$_2R^{10}$ and —NHCO$_2R^{10}$, wherein $R^{10}$ is phenyl, naphthyl, or phenyl or naphthyl substituted with one to three groups selected from $C_1$-$C_6$-alkyl, $C_6$-$C_{10}$ aryl, $C_1$-$C_6$-alkoxy and halogen.

The heteroaryl radicals which may be present as substituents on R, $R^1$, $R^2$, $R^3$, $R^4$, and $R^5$ include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$-$C_6$-alkyl, $C_1$-$C_6$-alkoxy, substituted $C_1$-$C_6$-alkyl, halogen, $C_1$-$C_6$-alkylthio, aryl, arylthio, aryloxy, $C_2$-$C_{15}$-alkoxycarbonyl, $C_2$-$C_{15}$-alkoxycarbonyloxy, and $C_2$-$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

Examples of alkyl carbonates include, but are not limited to, structure 2 resveratrol tris(alkyl carbonate), structure 3, hydroxytyrosol tris(alkyl carbonate), structure 4, 4-hydroxybenzyl alcohol di(alkyl carbonate), and structure 5, an ester of 4-(alkoxycarbonyloxy)-2-phenylethanol.

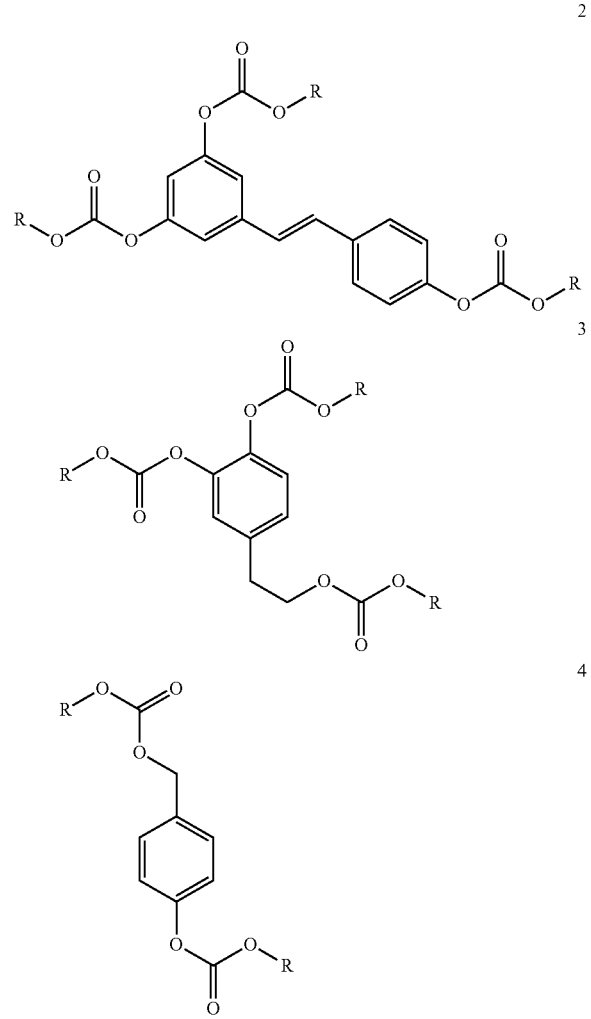

The novel process of our invention comprises the reaction of alcohol 6:

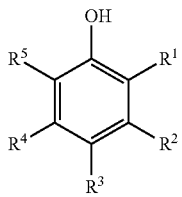

with a chloroformate, bromoformate, or dicarbonate to produce the alkyl carbonate of Formula 1.

The process is carried out without solvent or in an inert solvent chosen from cyclic or acyclic ether solvents, such as, diethyl ether, diisopropyl ether, tert-butyl methyl ether, or tetrahydrofuran; aromatic hydrocarbons, such as, benzene, toluene, or xylene; aliphatic or alicyclic saturated or unsaturated hydrocarbons, such as, hexane, heptane, cyclohexane, or limonene; halogenated hydrocarbons, such as, dichloromethane, dichloroethane, dibromoethane, tetrachloroethylene, or chlorobenzene; polar aprotic solvents, such as, acetonitrile, dimethyl formamide, or dimethyl sulfoxide; or mixtures thereof. In one embodiment of the invention, the no solvent is utilized. In another embodiment, dichloromethane, toluene, or mixtures thereof are utilized.

The process may be carried out at a temperature between about −100° C. and about 100° C. In another embodiment, the process may be carried out at a temperature between about −100° C. and the boiling point of the solvent. Other temperature ranges are from about 0° C. and 60° C. and from about 0° C. to about 50° C.

The amount of chloroformate, bromoformate or dicarbonate may be between about 0.85 and about 20 equivalents for each hydroxyl group on the compound of Formula 6. In another embodiment, the amount of chloroformate, bromoformate or dicarbonate may be between about 1 and about 10 equivalents or between about 1 and about 1.5 equivalents for each hydroxyl group being derivatized on the compound of Formula 6. The reaction can be run in the presence of an acid acceptor. Examples of acid acceptors include, but are not limited to, trialkylamines with between 3 and 15 carbon atoms or substituted or unsubstituted pyridines. The process may also be run in the presence of a catalyst. The catalyst may be a hypernucleophile such as N,N-dialkylaminopyridines or alkoxypyridines. The pressure for the reaction can range between about 1 torr to about 10 atm pressure. Another range is from about 200 torr to ambient pressure.

Carbonates of the present invention show an unexpected propensity to undergo enzymatic hydrolysis. This is particularly surprising, as analogous phenolic esters either do not cleave or are hydrolyzed very slowly under these enzymatic conditions. For example, both the tris(butyl carbonate) and the tris(methyl carbonate) of resveratrol (2, where R is n-butyl or methyl, respectively) undergo hydrolysis of the carbonate to afford dicarbonates, monocarbonates, and the parent triphenol upon treatment with a lipase in a biphasic mixture of toluene and aqueous pH 7 buffer. In the absence of the enzyme there is no observed hydrolysis. In contrast, the tripalmitate ester of resveratrol showed minimal hydrolysis under the same conditions. The anti-aging properties of the parent ingredients are likely linked to their behavior as antioxidants due to the phenolic substructures, so any derivatives of the ingredients will need to be cleavable in the skin to be efficacious. The enzymatic results indicate that the carbonates should be much more effective than the corresponding esters.

The parent phenols are insoluble in most organic solvents outside of methanol. The carbonates, in contrast, show a much broader solubility profile, which may help formulation and penetration into the skin. In addition, the parent phenols are somewhat unstable, and tend to turn brown upon storage. This is likely due to oxidative instability of the phenols, and the carbonate derivatization should improve upon this instability.

The alkyl carbonate product of the process may be isolated using methods known to those of skill in the art, e.g., extraction, filtration, or crystallization. The alkyl carbonate product of Formula 1 may be purified if necessary using methods known to those of skill in the art, e.g., extraction, chromatography, distillation, or crystallization.

The alkyl carbonates according to the present invention can be used in compositions, such as cosmetic compositions, skin care compositions and the like. The compositions can be useful, for example, for reducing skin roughness, fine lines, and wrinkles, improving photo-damaged skin, regenerating skin, reducing skin hyper-pigmentation, and reducing irritation and/or inflammatory reaction in skin.

Typical cosmetic and/or skin care compositions of the invention contain at least 0.001% by weight of the carbonates according to the present invention. For example, the compositions can contain from about 0.001% to about 20.0% by weight or from about 0.01% to about 10.0% by weight of the carbonates according to the present invention. Lower concentrations may be employed for less pronounced conditions, and higher concentrations may be employed with more acute conditions. Suggested ranges also depend upon any adjunct ingredients employed in the compositions.

The cosmetic and skin care compositions of the invention may also contain other skin conditioning ingredients in addition to carbonates. Such compositions may also contain other skin ingredients such as retinol, retinyl esters, tetronic acid, tetronic acid derivatives, hydroquinone, kojic acid, gallic acid, arbutin, α-hydroxy acids, and fatty acid esters of ascorbic acid. Such other ingredients are known to those of skill in the art.

Typically, topical application to skin sites is accomplished in association with a carrier. Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic). These same general ingredients can be formulated into a cream rather than a lotion, or into gels, or into solid sticks by utilization of different proportions of the ingredients and/or by inclusion of thickening agents such as gums or other forms of hydrophilic colloids.

The novel processes provided by the present invention are further illustrated by the following examples.

Example 1

Preparation of Resveratrol Tris(Methyl Carbonate) (Formula 2, R=Me)

Resveratrol (15 g; 65.7 mmol) was combined with dichloromethane (80 mL), and pyridine (18.8 g; 236 mmol; 3.6 equiv) was added dropwise. Methyl chloroformate (26.2 g; 278 mmol; 4.2 equiv) were added, and the reaction mixture was heated to reflux for 1 h, at which point HPLC analysis indicated five major peaks. Pyridine (6.3 g; 79.6 mmol; 1.2 equiv) and methyl chloroformate (8.8 g; 93.1 mmol; 1.4 equiv) were added and refluxed for 1 h, and this was repeated twice more until a single peak was observed by HPLC analysis. The mixture was diluted with ethyl acetate (250 mL) and washed with 3 M HCl (3×250 mL) and 5% sodium bicarbonate (3×250 mL). The organic solution was dried with sodium sulfate and concentrated to afford 26.6 g of crude hydroxytyrosol tris(methyl carbonate) (Formula 2, R=Me). The crude product was crystallized from 160 g of isopropyl alcohol to afford 21.4 g of resveratrol tris(methyl carbonate) (81%) which was >99% pure by HPLC analysis.

$^1$H NMR (Hydrogen-1 Nuclear Magnetic Resonance) (DMSO-$d_6$) δ 7.66 (d, 2H, J=8.7 Hz); 7.46 (d, 2H, J=2.2 Hz); 7.40 (d, 1H, J=16.4 Hz); 7.27 (d, 2H, J=8.7 Hz); 7.25 (d, 1H, J=16.6 Hz); 7.16 (t, 1H; J=2.1 Hz); 3.86 (br s, 6H); 3.84 (br s, 3H).

HPLC (High Performance Liquid Chromatography) (4.6× 150 mm Zorbax SB-C8 column [Agilent], 3.5µ thickness, 50:50 methanol:water (containing 0.1% trifluoroacetic acid) for 5 min, gradient to 100% methanol over 1 min, hold at 100% methanol for 11 min, detection at 294 nm): $t_R$ 8.65 min (2, R=Me); $t_R$ 3.3 min (resveratrol). LCMS: 402 ($M^+$ of 2, R=Me)

Example 2

Preparation of Resveratrol Tris(Butyl Carbonate) (2, R=n-Bu)

Resveratrol (10.0 g; 43.8 mmol) was dissolved in 50 mL (618 mmol; 14.1 equiv) of pyridine. The mixture was diluted with toluene (75 mL) and treated with n-butyl chloroformate (19.15 g; 140 mmol; 3.2 equiv) dissolved in 25 mL of toluene. An exotherm was noted during the addition, and cooling was applied (maximum temperature was 37° C.). The resulting white stirrable slurry was stirred overnight at ambient temperature, at which point HPLC analysis indicated one major product but several minor peaks (assumed to be mono- and di-carbonates). An additional 20% of butyl chloroformate (3.8 g) was added and the mixture was stirred overnight, at which point HPLC analysis indicated >94% of a single peak. The mixture was partitioned between 150 mL of ethyl acetate and 100 mL of water, and the water layer was decanted. The organic layer was washed with 3 M HCl (200 mL) and 5% sodium bicarbonate (100 mL), dried (MgSO4), then concentrated in vacuo with moderate heating to afford 22.96 g (99%) of Formula 2, R=n-Bu. $^1$H NMR was consistent with the anticipated structure and HPLC analysis indicated 97.1% purity with 0.7% resveratrol.

$^1$H NMR (CDCl$_3$) δ 7.49 (dt, 2H, J=8.7, 2.0 Hz); 7.22 (d, 2H, J=2.1 Hz); 7.19 (dt, 2H, J=8.7, 1.9 Hz); 7.08 (d, 1H, J=16.3 Hz); 7.01 (t, 1H, J=2.2 Hz); 6.97 (t, 1H; J=16.3 Hz);

4.275 (t, 4H, J=6.6 Hz); 4.265 (t, 2H, J=6.7 Hz); 1.8-1.65 (m, 6H); 1.53-1.37 (m, 6H); 0.98 (t, 9H, J=7.5 Hz).

HPLC-MS (4.6×150 mm Zorbax SB-C8 column [Agilent], 3.5µ thickness, 50:50 methanol:water (containing 0.1% trifluoroacetic acid) for 5 min, gradient to 100% methanol over 1 min, hold at 100% methanol for 11 min, detection at 294 nm): $t_R$ 9.18 min (2, R=n-Bu, $M^+$ 528); $t_R$ 8.8 min (resveratrol bis[butyl carbonate], $M^+$ 428); $t_R$ 8.5 min (resveratrol mono [butyl carbonate], $M^+$ 328); $t_R$ 3.3 min (resveratrol, $M^+$ 228).

Comparative Example 1

Preparation of Resveratrol Tripalmitate

Resveratrol (100 mg; 0.44 mmol) was dissolved in 1 mL of pyridine. Palmitoyl chloride (425 µL; 1.40 mmol; 3.2 equiv) was added with immediate solid formation noted. This mixture was stirred at ambient temperature for 12 h at which point HPLC analysis indicated no resveratrol present. The mixture was partitioned into ethyl acetate and water and the water layer was decanted. The top organic layer was washed sequentially with 1.5 M HCl (10 mL) and 5% sodium bicarbonate (10 mL), dried (MgSO4), and concentrated to afford 0.45 g (99%) of resveratrol tripalmitate.

$^1$H NMR (CDCl$_3$) δ 7.49 (br d, 2H, J=8.6 Hz); 7.15-6.95 (m, 6H); 6.80 (t, 1H; J=2.0 Hz); 2.55 (t, 6H, J=7.3 Hz); 1.5-1.2 (m, 78H); 0.88 (t, 9H, J=6.5 Hz).

HPLC (4.6×150 mm Zorbax SB-C8 column [Agilent], 3.5µ thickness, 50:50 methanol:water (containing 0.1% trifluoroacetic acid) for 5 min, gradient to 100% methanol over 1 min, hold at 100% methanol for 24 min, detection at 294 nm): $t_R$ 25.0 min (resveratrol tipalmitate); $t_R$ 3.3 min (resveratrol).

Example 3

Enzymatic Hydrolysis of Resveratrol Tris(Methyl Carbonate)

Resveratrol tris(methyl carbonate) (100 mg; 0.249 mmol) was dissolved in 2 mL of toluene. 2 mL of pH 7 buffer was added followed by 100 mg of Novozym 435 (immobilized Candida Antarctica lipase B). The mixture was stirred vigorously at ambient temperature for 22 h, at which point the HPLC analysis (equal volumes of both layers) indicated 23.75% resveratrol, 52.9% resveratrol mono(methyl carbonate), 15.8% resveratrol bis(methyl carbonate) and 7.0% resveratrol tris(methyl carbonate). After 3 days at ambient temperature HPLC analysis indicated 63.8% resveratrol, 35.1% resveratrol mono(methyl carbonate), 0.6% resveratrol bis(methyl carbonate), and no detectable resveratrol tris(butyl carbonate). A similar reaction run in the absence of enzyme showed no detectable hydrolysis after 3 days.

Example 4

Enzymatic Hydrolysis of Resveratrol Tris(Butyl Carbonate)

Resveratrol tris(butyl carbonate) (100 mg; 0.189 mmol) was dissolved in 2 mL of toluene. 2 mL of pH 7 buffer was added followed by 100 mg of Novozym 435 (immobilized Candida Antarctica lipase B). The mixture was stirred vigorously at ambient temperature for 1 days, at which point the top layer indicated 41% resveratrol bis(butyl carbonate) and 59% resveratrol tris(butyl carbonate). After 3 d at ambient temperature equal volumes of the top and bottom layers were analyzed by HPLC to indicate 35% resveratrol, 5% resveratrol mono(butyl carbonate), 41% resveratrol di(butyl carbonate), and 19% resveratrol tris(butyl carbonate).

Comparative Example 2

Enzymatic Hydrolysis of Resveratrol Tripalmitate

Resveratrol tripalmitate (100 mg; 0.11 mmol) was dissolved in 2 mL of toluene. 2 mL of pH 7 buffer was added followed by 100 mg of Novozym 435 (immobilized Candida Antarctica lipase B). The mixture was stirred vigorously at ambient temperature for 3 days to afford minimal hydrolysis with almost no resveratrol according to HPLC analysis: 89% resveratrol tripalmitate, 6.4% resveratrol dipalmitate, and 0.9% resveratrol.

Example 5

Preparation of 4-Hydroxybenzyl Alcohol bis(butyl carbonate)

4-Hydroxybenzyl alcohol (1.0 g; 8.06 mmol) was dissolved in 2 mL (24.7 mmol; 3 equiv) of pyridine. Toluene (9 mL) was added to afford a cloudy solution which was cooled in ice-water. Butyl chloroformate (2.42 g; 17.72 mmol; 2.2 equiv) was added and solid formation was immediate. The mixture was stirred at 0° C. for 1 h, at which point HPLC analysis indicated no 4-hydroxybenzyl alcohol and one major peak. The mixture was diluted with ethyl acetate and sequentially washed with water, 1.5 M HCl (20 mL), and 5% sodium bicarbonate (20 mL). The organic solution was dried with magnesium sulfate and concentrated to afford 2.52 g (96%) of 4-hydroxybenzyl alcohol bis(butyl carbonate).

$^1$H NMR (CDCl$_3$) δ 7.41 (dt, 2H, J=8.7, 2.7 Hz); 7.19 (dt, 2H, J=8.7, 2.6 Hz); 5.14 (s, 2H); 4.26 (t, 2H, J=6.7 Hz); 4.15 (t, 2H; J=6.6 Hz); 1.8-1.6 (m, 4H); 1.52-1.32 (m, 4H); 0.97 (t, 3H, J=7.3 Hz); 0.93 (t, 3H, J=7.3 Hz).

HPLC (4.6×150 mm Zorbax SB-C8 column [Agilent], 3.5µ thickness, 3:97 methanol:water (containing 0.1% trifluoroacetic acid) gradient to 40:60 methanol:water (containing 0.1% trifluoroacetic acid) over 20 min, gradient to 100% methanol over 5 min, hold at 100% methanol for 5 min, detection at 294 and 225 nm): $t_R$ 27.1 min (4-hydroxybenzyl alcohol bis[butyl carbonate]); $t_R$ 8.5 min (hydroxybenzyl alcohol)

Example 6

Enzymatic Hydrolysis of 4-Hydroxybenzyl Alcohol bis(butyl carbonate)

4-Hydroxybenzyl alcohol bis(butyl carbonate) (100 mg; 0.308 mmol) was dissolved in 1 mL of toluene. 1 mL of pH 7 buffer was added followed by 100 mg of Novozym 435 (immobilized Candida Antarctica lipase B). The mixture was stirred vigorously at ambient temperature for 1.5 h, at which point HPLC analysis (equal volumes of both layers) indicated 1.5% 4-hydroxybenzyl alcohol, 40 and 14% of each of the 4-hydroxybenzyl alcohol mono(butyl carbonate)s, and 41% 4-hydroxybenzyl alcohol bis(butyl carbonate). Note that the analysis for 4-hydroxybenzyl alcohol is inaccurate due to its insolubility in both toluene and water. After 21 h at ambient temperature HPLC analysis indicated very little mono- and bis-carbonates. A similar reaction run in the absence of enzyme showed no detectable hydrolysis after 3 days.

Example 7

Preparation of Hydroxytyrosol Tris(Methyl Carbonate) (3, R=Me)

Hydroxytyrosol (1.0 g; 6.49 mmol) was dissolved in 2.3 mL (24.7 mmol; 4.4 equiv) of pyridine. Toluene (9 mL) was added to afford a cloudy solution which was cooled in ice-water. Methyl chloroformate (2.45 g; 25.9 mmol; 4 equiv) was added, and solid formation was immediate. The mixture was stirred at 0° C. for 45 min and allowed to warm to ambient temperature over 6 h, at which point HPLC analysis indicated no hydroxytyrosol and one major peak. The mixture was diluted with ethyl acetate and sequentially washed with water, 1.5 M HCl (20 mL), and 5% sodium bicarbonate (20 mL). The organic solution was dried with magnesium sulfate and concentrated to afford 1.64 g (77%) of 3, R=Me, which was pure by $^1$H NMR analysis.

$^1$H NMR (CDCl$_3$) δ 7.24-7.11 (m, 3H); 4.34 (t, 2H, J=7.0 Hz); 3.905 (s, 3H); 3.90 (s, 3H); 3.77 (s, 3H); 2.96 (t, 2H, J=6.9 Hz).

HPLC (4.6×150 mm Zorbax SB-C8 column [Agilent], 3.5μ thickness, 3:97 methanol:water (containing 0.1% trifluoroacetic acid) gradient to 40:60 methanol:water (containing 0.1% trifluoroacetic acid) over 20 min, gradient to 100% methanol over 5 min, hold at 100% methanol for 5 min, detection at 294 and 225 nm): $t_R$.25.2 min (3, R=Me); $t_R$ 8.5 min (hydroxytyrosol).

Comparative Example 3

Preparation of Hydroxytyrosol Trihexanoate

Hydroxytyrosol (1.00 g; 6.49 mmol) was dissolved in 2.3 mL of pyridine (28.4 mmol; 4.4 equiv). The mixture was diluted with toluene (9 mL) and cooled in ice-water. Hexanoyl chloride (2.99 mL; 21.4 mmol; 3.3 equiv) was added with immediate solid formation noted. This mixture was allowed to warm to ambient temperature overnight at which point HPLC analysis indicated no hydroxytyrosol present and one major peak. The mixture was partitioned into ethyl acetate and water and the water layer was decanted. The top organic layer was washed sequentially with 1.5 M HCl (20 mL) and 5% sodium bicarbonate (20 mL), dried (MgSO4), and concentrated to afford 2.86 g (98%) of hydroxytyrosol trihexanoate which contained 1.9% residual hydroxytyosol.

$^1$H NMR (CDCl$_3$) δ 7.1-7.0 (m, 3H); 4.27 (t, 2H, J=7.0 Hz); 2.92 (t, 2H, J=6.9 Hz); 2.52 (t, 2H, J=7.4 Hz); 2.44 (t, 2H, J=7.4 Hz); 2.28 (t, 2H, J=7.3 Hz); 1.8-1.55 (m, 6H); 1.45-1.25 (m, 12H), 0.97-0.85 (m, 9H).

HPLC (4.6×150 mm Zorbax SB-C8 column [Agilent], 3.5μ thickness, 3:97 methanol:water (containing 0.1% trifluoroacetic acid) gradient to 40:60 methanol:water (containing 0.1% trifluoroacetic acid) over 20 min, gradient to 100% methanol over 5 min, hold at 100% methanol for 5 min, detection at 294 and 225 nm): $t_R$.27.8 min (hydroxytyrosol trihexanoate); $t_R$ 8.5 min (hydroxytyrosol).

Example 8

Enzymatic Hydrolysis of Hydroxytyrosol Tris(Methyl Carbonate)

Hydroxytyrosol tris(methyl carbonate) (3, R=Me, 100 mg; 0.305 mmol) was dissolved in 2 mL of toluene. 2 mL of pH 7 buffer was added followed by 100 mg of Novozym 435 (immobilized Candida Antarctica lipase B). The mixture was stirred vigorously at ambient temperature for 24 h, at which point HPLC analysis (equal volumes of both layers) indicated 74% hydroxytyrosol, 1.5% mono- and di-carbonates, and 17% 3 (R=Me). After 48 h at ambient temperature HPLC analysis indicated 92% hydroxytyrosol, 5% mono- and di-carbonates, and 3% 3 (R=Me). A similar reaction run in the absence of enzyme showed no detectable hydrolysis to hydroxytyrosol after 2 days.

Comparative Example 4

Enzymatic Hydrolysis of Hydroxytyrosol Trihexanoate

Hydroxytyrosol trihexanoate containing 1.9% hydroxytyrosol by HPLC analysis (100 mg; 0.22 mmol) was dissolved in 2 mL of toluene. 2 mL of pH 7 buffer was added followed by 100 mg of Novozym 435 (immobilized Candida Antarctica lipase B). The mixture was stirred vigorously at ambient temperature for 48 h to afford 72.3% hydroxytyrosol trihexanoate, 18.7% 3,4-di(hexanoyl)phenylethanol, and 2.5% hydroxytyrosol.

Example 9

Preparation of 4-(n-Butoxycarbonyloxy)-2-phenethyl Linoleate

Tyrosol linoleate (4-hydroxy2-phenethyl linoleate) (2.0 g; 4.99 mmol) was dissolved in 2 mL (24.7 mmol; 3 equiv) of pyridine. Toluene (9 mL) was added to afford a cloudy solution which was cooled in ice-water. Butyl chloroformate (2.42 g; 17.72 mmol; 2.2 equiv) was added, and solid formation was immediate. The mixture was allowed to warm to ambient temperature and stirred for 6 h, at which point HPLC analysis indicated <2% tyrosol linoleate and one major peak. The mixture was diluted with ethyl acetate and sequentially washed with water, 1.5 M HCl (20 mL), and 5% sodium bicarbonate (20 mL). The organic solution was dried with magnesium sulfate and concentrated to afford 2.75 g of 4-(n-butoxycarbonyloxy)-2-phenethyl linoleate.

$^1$H NMR (CDCl$_3$) δ 7.22 (d, 2H, J=8.5 Hz); 7.10 (d, 2H, J=8.5 Hz); 5.35 (m, 4H); 4.27 (t, 2H, J=6.9 Hz); 4.24 (t, 2H; J=6.7 Hz); 2.93 (t, 2H, J=7.0 Hz); 2.77 (t, 2H, J=5.8 Hz); 2.28 (t, 2H, J=7.4 Hz); 2.1-2.0 (m, 4H); 1.8-1.65 (m, 2H); 1.65-1.25 (m, 20H); 0.97 (t, 3H, J=7.3 Hz); 0.89 (t, 3H, J=6.9 Hz).

HPLC (4.6×150 mm Zorbax SB-C8 column [Agilent], 3.5μ thickness, 10:90 methanol:water (containing 0.1% trifluoroacetic acid) for 20 min, detection at 225 nm): $t_R$ 10.8 min 4-(n-butoxycarbonyloxy)-2-phenethyl linoleate); $t_R$ 5.2 min (tyrosol linoleate).

That which is claimed is:

1. An alkyl carbonate selected from the group consisting of structure 2, resveratrol tris(alkyl carbonate); and structure 3, hydroxytyrosol tris(alkyl carbonate)

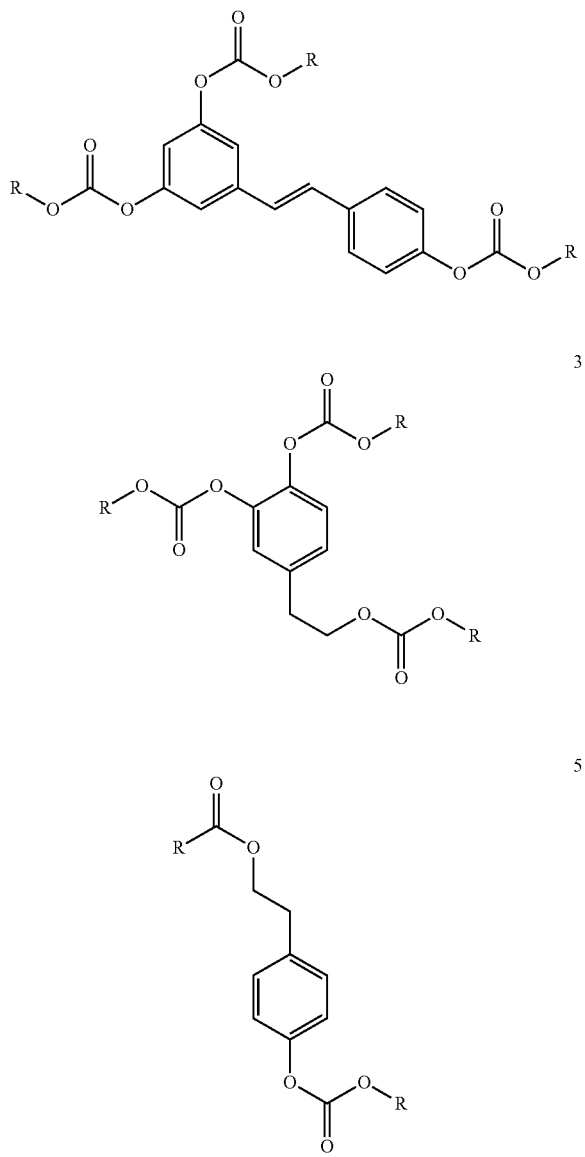

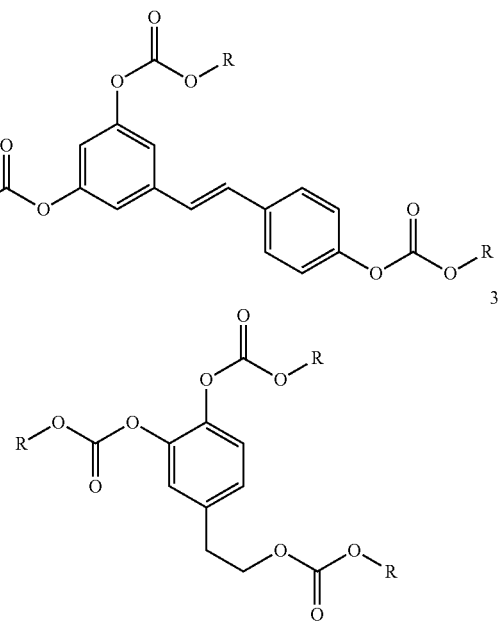

wherein R is selected from, branched- or straight-chain $C_1$-$C_{22}$ alkyl wherein said branched-or straight-chain $C_1$-$C_{22}$ alkyl is unsubstituted and saturated.

2. The alkyl carbonate according to claim 1 wherein said alkyl carbonate is structure 2, resveratrol tris(alkyl carbonate).

3. The alkyl carbonate according to claim 1 wherein said alkyl carbonate is structure 3, hydroxytyrosol tris(alkyl carbonate).

4. The alkyl carbonate according to claim 1 wherein said alkyl carbonate is an $C_2$-$C_{22}$ saturated ester of structure 5, 4-(alkoxycarbonyloxy)-2-phenylethanol.

5. The process of producing an alkyl carbonate selected from the group consisting of structure 2, resveratrol tris(alkyl carbonate); and structure 3, hydroxytyrosol tris(alkyl carbonate) wherein R is selected from branched- or straight-chain $C_1$-$C_{22}$ alkyl, wherein said branched- or straight-chain $C_1$-$C_{22}$ alkyl is unsubstituted and saturated comprising reacting at least one alcohol selected from the group consisting of resveratrol and hydroxytyrosol with a chloroformate, bromoformate, or dicarbonate.

6. The process according to claim 5 wherein said process is carried out without solvent or in an inert solvent selected from at least one of the group consisting of cyclic ethers or acyclic ethers; aromatic hydrocarbons; aliphatic or alicyclic saturated or unsaturated hydrocarbons; halogenated hydrocarbons; and polar aprotic solvents.

7. The process according to claim 6 wherein said inert solvent is selected from at least one of the group consisting of diethyl ether, diisopropyl ether, tert-butyl methyl ether, tetrahydrofuran, benzene, toluene, xylene, hexane, heptane, cyclohexane, limonene, dichloromethane, dichloroethane, dibromoethane, tetrachloroethylene, chlorobenzene, acetonitrile, dimethyl formamide, and dimethyl sulfoxide.

8. The process according to claim 5 wherein said process is carried out at a temperature between about −100° C. and about 100° C.

9. The process according to claim 8 wherein said process is carried out at a temperature between about 0° C. to about 50° C.

10. The process according to claim 5 wherein the amount of said chloroformate, bromoformate or dicarbonate is in the range between about 0.85 and about 20 equivalents for each hydroxyl group on said alcohol.

11. The process according to claim 5 wherein said reaction is conducted in the presence of an acid acceptor.

12. The process according to claim 5 wherein said reaction is conducted in the presence of a catalyst.

13. A composition comprising said alkyl carbonate of claim 1.

14. The composition according to claim 13, wherein said composition is a cosmetic composition.

15. The cosmetic composition according to claim 14 wherein the amount of said alkyl carbonate is at least 0.001% by weight.

* * * * *

UNITED STATES PATENT AND TRADEMARK OFFICE
CERTIFICATE OF CORRECTION

PATENT NO. : 8,613,940 B2  Page 1 of 1
APPLICATION NO. : 12/975562
DATED : December 24, 2013
INVENTOR(S) : Boaz It is certified that error appears in the above-identified patent and that said Letters Patent is hereby corrected as shown below:

In the Claims

Claim 1, Column 13, lines 31 – 47 structure 5 " 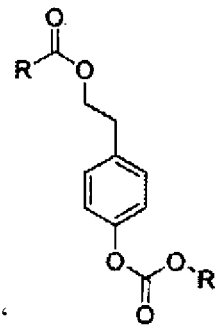 " should be deleted; lines 61 – 63 should cancel text beginning with "4. The alkyl carbonate" to and ending "2-phenylethanol."

Signed and Sealed this
Thirtieth Day of December, 2014

Michelle K. Lee
*Deputy Director of the United States Patent and Trademark Office*